United States Patent
Stewart et al.

(10) Patent No.: US 9,999,588 B1
(45) Date of Patent: Jun. 19, 2018

(54) TOPICAL SKIN CARE FORMULATIONS AND METHODS OF USING SAME

(71) Applicants: Lisa Stewart, Brecksville, OH (US); Ara Asadorian, Penisula, OH (US)

(72) Inventors: Lisa Stewart, Brecksville, OH (US); Ara Asadorian, Penisula, OH (US)

(73) Assignee: Lisa Stewart, Brecksville, OH (US)

( * ) Notice: Subject to any disclaimer, the term of this patent is extended or adjusted under 35 U.S.C. 154(b) by 0 days. days.

(21) Appl. No.: 15/044,358

(22) Filed: Feb. 16, 2016

Related U.S. Application Data

(60) Provisional application No. 62/116,606, filed on Feb. 16, 2015.

(51) Int. Cl.
| | |
|---|---|
| *A61K 8/97* | (2017.01) |
| *A61K 8/02* | (2006.01) |
| *A61K 8/49* | (2006.01) |
| *A61K 8/37* | (2006.01) |
| *A61Q 19/00* | (2006.01) |

(52) U.S. Cl.
CPC .............. *A61K 8/97* (2013.01); *A61K 8/0241* (2013.01); *A61K 8/375* (2013.01); *A61K 8/4973* (2013.01); *A61Q 19/00* (2013.01); *A61Q 19/007* (2013.01); *A61K 2800/28* (2013.01); *A61K 2800/30* (2013.01); *A61K 2800/31* (2013.01); *A61K 2800/41* (2013.01); *A61K 2800/49* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 8,178,106 B2 | 5/2012 | Hines et al. | |
| 2002/0142019 A1* | 10/2002 | Kuhnau | A61K 8/46 424/401 |
| 2004/0018244 A1* | 1/2004 | Piterski | A61K 8/64 424/535 |
| 2014/0363476 A1* | 12/2014 | Thomas | A61K 8/02 424/401 |

FOREIGN PATENT DOCUMENTS

WO   WO 2014020219 A1 *   2/2014   ............. A61K 8/676

OTHER PUBLICATIONS

Navarro, S.M., et al, WO2014020219A1 English translation. acessed from:"https://www.google.com.gt/patents/WO2014020219A1?cl=en&dq=2014020219&hl=en&sa=X&ved=0ahUKEwimkf7K3-jVAhUl7lMKHa79CWkQ6AEILDAB", printed on Aug. 21, 2017, pp. 1-17.*
Harris, S., "My Top 5 Exfoliators & How I Cleared Up My Acne!", accessed from:http://www.shaaanxoblogs.com/2014/06/my-top-5-exfoliators-how-i-cleared-up.html, Jun. 30, 2014, pp. 1-23.*

* cited by examiner

*Primary Examiner* — Michael G Hartley
*Assistant Examiner* — Lance W Rider
(74) *Attorney, Agent, or Firm* — Pearne & Gordon LLP

(57) ABSTRACT

A natural and dual-functioning topical skin care composition for exfoliating and moisturizing the skin. The compositions include undissolved, water-soluble Camu Camu particles as an exfoliant in a pharmaceutically acceptable carrier. The compositions are anhydrous or substantially free of water to retain the exfoliant Camu Camu particles in the composition as it is applied and rubbed onto the skin. The compositions provide a rinse-free way to exfoliate the skin with the application of minute amounts of water to dissolve the vitamin C enriched Camu Camu particles of the compositions that may then be absorbed into the skin.

15 Claims, No Drawings

TOPICAL SKIN CARE FORMULATIONS AND METHODS OF USING SAME

This application claims the benefit of U.S. provisional application Ser. No. 62/116,606 filed Feb. 16, 2015, the contents of which are incorporated herein in their entirety by reference.

FIELD

The present disclosure relates to compositions that can be used to improve the skin, and more particularly, anhydrous compositions that both exfoliate and moisturize the skin wherein undissolved Camu Camu particles function as the exfoliant in the compositions and can be absorbed into the skin.

BACKGROUND

Skin care products often include unnatural and toxic ingredients. These undesirable ingredients are added, in part, to promote the appearance of the products. In some cases, because most skin care products contain water, preservatives, such as parabens, are added to ensure the stability of the product over time and prevent bacteria growth. In another example, oil and water formulations may contain emulsifiers, which can irritate and be absorbed by the skin. Accordingly, the inclusion of such unnatural and toxic ingredients results in products that can be irritating to the skin and unnecessarily introduce harmful toxins into the body.

There is a need for skin care products that contain all natural ingredients that are not harmful to the body. The preset invention overcomes deficiencies in the art by providing skin care compositions that can be used to exfoliate and moisturize the skin, wherein the compositions do not contain unnatural and toxic ingredients. The product of the present invention has been proven to lighten, tighten, hydrate and exfoliate the skin upon application.

SUMMARY

In a first aspect, there is a topical skin care composition that includes about 5 weight percent to about 20 weight percent of Camu Camu particles as an exfoliant, about 0.5 weight percent to about 15 weight percent of a surfactant, and about 70 weight percent to about 90 weight percent of a carrier.

In an example of aspect 1, the composition is in the form of a lotion, an ointment, a cream, a paste, a mask or a semi-solid.

In another example of aspect 1, the composition contains less than 0.5 weight percent of water, and preferably less than 0.1 weight percent of water.

In another example of aspect 1, the composition is anhydrous and free of water.

In another example of aspect 1, the pH of the composition is in the range of about 2 and about 6.

In another example of aspect 1, the composition is free of preservatives, for example, synthetic preservatives or parabens.

In another example of aspect 1, the composition is free of alcohols.

In another example of aspect 1, the composition is free of materials selected from the group of synthetic soaps, synthetic thickeners, synthetic surfactants, and combinations thereof.

In another example of aspect 1, the composition is free of a second exfoliant such that the Camu Camu particles represent the sole exfoliant in the composition.

In another example of aspect 1, the Camu Camu particles having an average particle size in the range of about 50 to about 1,000 microns.

In another example of aspect 1, the Camu Camu particles having an average particle size of less than about 500 microns.

In another example of aspect 1, the Camu Camu particles having a Vitamin C content of greater than about 10 weight percent, and preferably greater than 20 weight percent.

In another example of aspect 1, the pharmaceutically acceptable carrier includes shea butter.

In another example of aspect 1, the pharmaceutically acceptable carrier includes a mixture of ingredients, the mixture including at least shea butter and oils, for example, jojoba oil.

In another example of aspect 1, the composition further includes about 0.1 wt % to about 5 wt % of a pH adjustment agent, wherein the pH of the composition is in the range of about 3 and about 5.

In another example of aspect 1, a method for exfoliating the skin of a subject in need thereof includes topically administering the composition onto the skin of the subject. The method can further include rubbing the composition onto the skin to exfoliate the skin with the Camu Camu particles.

In another example of aspect 1, exfoliating the skin can include the step of applying water to the skin of the subject after administering the composition, the water being effective to dissolve the Camu Camu particles of the composition, and preferably less than necessary to rinse the composition from the skin.

The first aspect may be provided alone or in combination with any one or more of the examples of the first aspect discussed above.

In a second aspect, there is a topical skin care composition that includes about 10 weight percent to about 20 weight percent of undissolved, water-soluble Camu Camu particles as the sole exfoliant, the Camu Camu particles having an average particle size in the range of about 50 to about 1,000 microns, about 0.5 weight percent to about 15 weight percent of a naturally-derived surfactant, about 70 weight percent to about 90 weight percent of a moisturizing pharmaceutically acceptable carrier, about 0.1 wt % to about 5 wt % of a pH adjustment agent, and, optionally, about 0.1 weight percent to about 0.5 weight percent of a fragrance. The composition is anhydrous and has a pH of less than about 5.

In an example of aspect 2, the Camu Camu particles having a Vitamin C content of greater than about 10 weight percent, and preferably greater than about 20 weight percent.

In another example of aspect 2, the composition is dual functioning such that it is capable of exfoliating and moisturizing the skin upon being topically administered to the skin of a subject. The composition is preferably a non-rinse composition that can be absorbed and dry on the skin after application, wherein water is used during application as a solvent for the Camu Camu particles.

In another example of aspect 2, the composition is free of preservatives and alcohols.

In another example of aspect 2, the composition only includes the Camu Camu particles, carrier, surfactant, pH adjusting agent, and fragrance. The carrier can be a combination of one or more butters and one or more oils.

The second aspect may be provided alone or in combination with any one or more of the examples of the first or second aspects discussed above.

In a third aspect, there is a topical skin care composition that includes at least about 10 wt %, e.g., about 10 wt % to about 20 wt %, of undissolved, water-soluble Camu Camu particles having an average particle size of less than about 1,000 microns, the Camu Camu particles having a Vitamin C content of greater than about 10 or 20 wt %; at least about 70 wt % of a moisturizing pharmaceutically acceptable carrier, the carrier comprising a plant-based butter and a plant-based oil; and about 0.1 to about 5 wt % of an amino acid, the amino acid being a component not present in the Camu Camu particles and is a pH adjuster. The composition has a pH of less than about 5, contains less than about 0.1 weight percent of water or is anhydrous, and is free of preservatives and alcohols. Preferably, the Camu Camu particles are the sole exfoliant in the composition.

In an example of aspect 3, the carrier further includes one or more waxes, for example, a plant-based wax.

The third aspect may be provided alone or in combination with any one or more of the examples of the first, second or third aspects discussed above.

DETAILED DESCRIPTION

Herein, when a range such as 5-25 (or 5 to 25) is given, this means preferably at least or more than 5 and, separately and independently, preferably not more than or less than 25. In an example, such a range defines independently at least 5, and separately and independently, not more than 25. As used herein, weight percent (i.e. wt. % or wt %) is based on the total weight of the topical skin care compositions unless specified otherwise.

Skin appearance can be desirably enhanced by the topical skin care compositions of the present disclosure. Environmental damage to the skin can occur over time and result in the skin having an uneven skin tone, or being dry, cracked and wrinkled. Products on the market sold to improve the appearance of skin are packed full of unnecessary and unnatural ingredients that can carry drawbacks such as skin irritation.

The topical skin care compositions of the present disclosure are preferably substantially anhydrous or anhydrous (non-aqueous) such that the compositions do not include or are free of water (i.e. 0 wt. %) or, for example, contain less than about 1, 0.5, 0.2 or 0.1 weight percent water based on the total weight of the composition. The anhydrous compositions are preferably not oil free, for instance, the base material or pharmaceutically acceptable carrier can contain one or more oils.

The compositions can be applied to any skin area, for example, the body, feet and face. To apply the compositions, the compositions can be in the form of a lotion, an ointment, a cream, a paste, a mask, a semi-solid or combinations thereof. Viscosity of the compositions can be adjusted as desired, for instance, the compositions preferably have a viscosity in the range of 5,000 to 50,000 cps, e.g., as measured on a Brookfield Viscometer using a spindle at 25° C. To adjust the viscosity of the pharmaceutically acceptable carrier, one or more oils can be added, which can reduce the viscosity.

The topical skin care compositions include a base material or pharmaceutically acceptable carrier, also referred to as the carrier herein. The carrier material provides a vehicle for applying other ingredients in the compositions, e.g., the undissolved Camu Camu particle exfoliator. The carrier can represent the bulk of the composition, for example, the carrier can be present in the range of about 65 to about 95 weight percent, about 70 to about 90 weight percent, or about 75, 80 or 85 weight percent.

The carrier can include one or more components that moisturize the skin when the compositions are used, for example, the carrier can be a moisturizing carrier. In one or more embodiments, the carrier can include at least one moisturizer, for example, a butter or plant-based butter (vegetable butter). For instance, the carrier can include cocoa butter, shea butter, almond butter, soy butter, mango butter, pistachio butter, sal butter, macadamia nut butter, avocado butter, and combinations thereof.

In one or more embodiments, the carrier can include one or more oils. Oils can include plant-based oils and/or mineral oils, for example, vegetable oils, coconut oil, sesame oil, almond oil, corn oil, soybean oil, sunflower oil, jojoba oil, grape seed oil, olive oil, partially hydrogenated palm oil, and combinations thereof. Oils can be used as desired to adjust the viscosity of the carrier. In one embodiment, the carrier material can be free of oils such that the topical skin care compositions are oil free.

In one or more embodiments, the carrier can include one or more waxes, for example, plant waxes, floral waxes, berry waxes, and combinations thereof. The waxes can contain natural moisturizers or phospholipids, for example, those that melt at body temperature and promote moistening of the skin.

In one or more embodiments, the carrier can include a mixture of two or more components selected from butters, oils and waxes. For example, the carrier can include at least one butter component and at least one oil component. In another example, the carrier can include two or more butter components and at least one oil component. In one or more embodiments, the carrier can include three or more components selected from butters, oils and waxes. For example, the carrier can include at least one butter component, at least one oil component and at least one wax component.

The compositions include undissolved, water-soluble Camu Camu (botanical name *Myrciaria dubia*) particles as an exfoliator, for example, the compositions can consist of a particulate phase that is Camu Camu particles suspended in the carrier. The Camu Camu particles are preferably evenly distributed in the carrier and other ingredients of the compositions. The Camu Camu particles can be mixed and formulated by conventional methods as known in the art.

The Camu Camu particles can be the only exfoliator ingredient or particulate phase in the compositions. The Camu Camu particles are soluble in water and are added to the water-free carrier material as a dry particulate material. Because Camu Camu is present as an undissolved particulate exfoliant in the compositions, the compositions are desirably substantially anhydrous or water free such that when the compositions are applied to the skin the Camu Camu particles can effectively exfoliate the skin as the compositions are rubbed onto the skin. Thus, as the exfoliant in the compositions, the amount and size of the Camu Camu particles is selected to deliver an effective exfoliating component in the compositions. It is appreciated that one or more components in the compositions can include residual water although the overall water presence in the composition is minimal and insufficient to dissolve the Camu Camu particulate phase.

The Camu Camu particles can be present in the compositions from about 5 to about 20 weight percent, about 8 to 18 weight percent, or about 10, 12, 14, or 16 weight percent.

In one or more embodiments, the Camu Camu particles are present in an amount of at least 8, 10, 12, 14, 16 or 18 weight percent.

As the exfoliator ingredient, the Camu Camu particles can have an average particle size (i.e. diameter) in the range of about 50 to about 1,000 microns, for example, at least about 100, 200, 300, 400 or 500 microns. In one embodiment, the Camu Camu particles can have a particle size distribution such that at least 90 to 99 percent of the particles have a diameter less than about 1,000, 800, 600, 500 or 400 microns.

The Camu Camu particles can deliver ascorbic acid (Vitamin C) to the skin during or following exfoliation of the skin, for example, upon the addition of water to dissolve the Camu Camu particles. The Camu Camu particles can have a Vitamin C content in the range of about 10 to about 30 weight percent, or about 15, 20 or 25 weight percent, based on the total weight of the Camu Camu particles (not the total weight of the composition). In one or more embodiments, the Camu Camu particles have a Vitamin C content of greater than about 10, 12, 14, 16, 18 or 20 weight percent.

The Camu Camu particulate exfoliant provides many beneficial properties. Vitamin C or ascorbic acid is an antioxidant, a substance that prevents oxidation of the body's cells by reactive molecules like free radicals and reactive oxygen species (ROS). Ascorbic acid can function to mitigate damage caused by free radicals in the body. Applying the exfoliating compositions containing the Camu Camu particles to the skin can first exfoliate the skin followed by absorption of the Camu Camu particles, for example when water is applied to dissolve the particle, to help protect from the aging effects of free radicals. The vitamin C enriched Camu Camu particles can promote increase of collagen levels in the dermal tissue, which can aid the skin to gain elasticity and reduce wrinkles. The particles can brighten and lighten the skin, which can address hyperpigmentation, for example, as caused by the sun or hormone imbalances. In another example, the particles can enhance immune systems.

The Camu Camu particles can further include other nutrients such as proteins, amino acids and B-vitamins including niacin (vitamin B3), riboflavin (vitamin B2) and thiamin (vitamin B1). Malic acid and citric acid can improve skin texture and reduce fine lines and wrinkles, for example, these components can promote shedding of the outer layers of the epidermis by loosening the "intercellular cement" that holds them together. This effectively thins the epidermis, which improves skin texture and the ability of skin to reflect light, thereby increasing skin luminescence and giving it a brighter, more toned appearance.

The amino acids and proteins in the Camu Camu particles can offer multiple benefits that promote skin health. For example, these compounds are hygroscopic and function as effective humectants on the skin that bind water and increase skin moisture content. Amino acids and proteins are a part of the skin's own natural moisturizing factor. The factors are water soluble, and repeated contact with water will leach them from the skin, making the skin drier until the factors can be replaced.

Amino-acid enriched Camu Camu particles have a high affinity for the skin environment and therefore deposit effectively into upper skin layers to deliver their effects. They are also compatible with health skin pH levels and have natural buffering capacity. The application of the particles that include the proteins and amino acids to the skin aids in the replenishment of NMF and supports skin hydration. As a result, the particles can help correct visible signs of dryness like roughness, scaling, tightness or dullness. The ability of the particles to further increase moisture levels can result in the skin appearing plumper and smoother, thereby visibly reducing the look of fine lines and wrinkles.

Minerals and electrolytes like calcium, magnesium and potassium are also present in the particles. The Camu Camu particles can further include flavonoids, for example, anthocyanins, flavonols, catechins, ellagic acid, gallic acid and rutin, which function as antioxidants on the skin. Flavonoids may affect anti-inflammatory mechanisms through inhibition of reactive oxygen species (ROS) that can cause cellular DNA damage, leading to premature collagen and elastin degradation in the skin. They also have been shown to inhibit pro-inflammatory enzymes upstream of ROS production such as cyclooxygenase and lipoxygenase. By being potent antioxidants and anti-inflammatory agents, the flavonoid compounds in the Camu Camu particles are helpful for providing anti-aging benefits.

In one or more embodiments, the compositions can include one or more surfactants. The total surfactant content present in the compositions can be in the range of about 0.5 to about 15 weight percent, about 1 to about 10 weight percent, or about 2, 3, 4, 5, 6 or 8 weight percent. In another embodiment, the surfactant can be present in an amount less than about 10, 8, 6, 5 or 4 weight percent. It is preferably that the surfactant be a natural component. The surfactant can further be non-toxic and/or biodegradable. In one example, the surfactant can include oleoyl sarcosine, e.g., Hamposyl® O. Oleoyl sarcosine is a FDA-approved food additive that is biodegradable and not toxic. Other examples include natural cosmetic surfactants as known in the art.

The compositions can include a fragrance or be fragrance free. Fragrance is not considered to be an essential component of the topical skin care compositions. Optionally, when a fragrance is included, the fragrance can be present in the compositions from about 0.1 to about 0.5 weight percent, for example, at least about 0.1, 0.2 or 0.3 weight percent. Any suitable fragrance can be used to impart a desirable scent to the compositions.

The compositions can optionally include one or more dyes, which can be present at less than 10 weight percent. For example, one or more dyes can be present in the range of 0.1 to A dye can be added to provide a make-up quality to the compositions, for instance, for applying the compositions to the face, such as an eye cream or the like.

The compositions are preferably free of preservatives and alcohols. For instance, the compositions do not include parabens, such as methylparaben, propylparaben, or a mixture of methylparaben and propylparaben. The compositions are also preferably free of other synthetic components, for example, synthetic soaps, synthetic thickeners, synthetic surfactants, and combinations thereof.

The compositions are generally acidic and have a pH of less than 7. For example, the compositions can have a pH in the range of about 2 to about 6, or about 2.5 to about 4.5, or about 3, 3.5 or 4. In another example, the compositions have a pH of less than about 6, 5, 4 or 3.

The pH of the compositions can be adjusted as known in the art. For instance, one or more pH adjusting agents can be added to the compositions. The one or more pH adjusting agents can be present in the compositions in a range of about 0.1 to about 5 weight percent, about 0.5 to about 4 weight percent, or about 1, 1.5, 2, 2.5, 3 or 3.5 weight percent. In another example, the one or more pH adjusting agents can be present in an amount of less than about 4, 3 or 2 weight percent. The pH adjusting agent can be those as known in the art. In one example, the pH adjusting agent can be an amino acid, which can further promote the benefits discussed herein. An amino acid can be, for example, glycine, arginine and the like.

In one embodiment, the composition can be an anhydrous thick cream that includes about at least 80 weight percent carrier, at least 12 weight percent of Camu Camu particles, at least 2 weight percent of a surfactant, less than 3 weight percent of a pH adjuster, and less than 0.5 weight percent of a fragrance, wherein the composition has a pH of less than about 5. Preferably, the Camu Camu particles have an average particle size (diameter) of less than 500 microns.

As discussed above, the compositions can be applied to the skin. The compositions can be rubbed onto the skin, for example, with one's hand or with a conventional application tool, such as a cloth, scrub brush or mechanical scrubbing device.

As the compositions are rubbed onto the skin, the undissolved Camu Camu particles gently exfoliate the skin as the carrier material, inclusive moisturizing components, e.g., butters and/or oils, moisturizes the skin. After a period of exfoliating and moisturizing the skin, water can be periodically applied to the composition, now spread out over the skin. The water can be applied by hand or with the aid of a spray device, such as a mister.

The applied water will dissolve the Camu Camu particles present on the skin, wherein water can be added in an amount to entirely dissolve the Camu Camu particles such that no exfoliating ingredient remains. As the person continues to rub the wetted composition onto the skin, the composition and dissolved Camu Camu particles is absorbed by the skin leaving the skin moisturized and exfoliated.

In one embodiment, a method of exfoliating and moisturizing the skin includes the following steps. The topical skin care composition is applied to the skin and moved across the surface of the skin (e.g., hand motion, by a device, rubbing or massaging onto the skin) to exfoliate and moisturize the skin by contacting the abrasive Camu Camu particles and carrier material with the skin surface. Dead skin cells and loose skin layers are dislodged and scrubbed away from underlying skin layers and cells. During the exfoliating step, water is applied at one or more points subsequent to the compositions being moved across the skin surface. In an example, water is applied after the composition is rubbed onto the skin.

Water is applied in an amount to begin dissolving the water-soluble Camu Camu particles in the composition. In an example, water can be added in a sufficient amount to dissolve all of or a majority of the Camu Camu particles in the composition. The composition, as diluted with the added water, can be further rubbed or moved across the skin surface to absorb the dissolved Camu Camu particles into the skin.

The method does not require and can be absent of a rinsing step that washes and removes the composition from the skin. Thus, water can be added in an amount to dissolve the Camu Camu particles but less than needed to wash or rinse the composition from the skin. The composition absorbs and dries on the skin to leave it moisturized and exfoliated.

The present discloses provides a dual functioning exfoliating and moisturizing product that does not require rinsing off of the skin. The natural and safe compositions can be left on the skin without introducing synthetic and toxic components into a person. The non-rinse compositions promote ease of use and are efficient at delivering high amounts of beneficial ingredients to the skin. The active exfoliating agent, Camu Camu particles, function to exfoliate the skin and enrich the skin when dissolved and absorbed, which imparts the skin with high levels of vitamin C. The invented compositions do not leave a greasy or gritty residue on the skin and are safe, biodegradable and edible.

While various aspects and embodiments have been disclosed herein, other aspects and embodiments will be apparent to those skilled in the art. The various aspects and embodiments disclosed herein are for purposes of illustration and are not intended to be limiting.

The invention claimed is:

1. A topical skin care composition consisting essentially of:
   a. about 10 wt % to about 20 wt % of undissolved, water-soluble Camu Camu particles as an exfoliant, the Camu Camu particles having an average particle size in the range of about 50 to about 1,000 microns;
   b. about 0.5 wt % to about 15 wt % of a naturally-derived surfactant;
   c. about 70 wt % to about 90 wt % of a moisturizing plant-based pharmaceutically acceptable carrier;
   d. about 0.1 wt % to about 5 wt % of a pH adjustment agent;
   wherein the composition is anhydrous and has a pH of less than about 5 and the composition is free of any added preservatives and alcohols.

2. The topical skin care composition of claim 1, the Camu Camu particles having a Vitamin C content of greater than about 20 wt %.

3. The topical skin care composition of claim 1, the composition being a dual-functioning composition for exfoliating and moisturizing the skin when the composition is topically administered to the skin.

4. The topical skin care composition of claim 1, the pH adjustment agent being an amino acid.

5. The topical skin care composition of claim 4, the amino acid being arginine.

6. The topical skin care composition of claim 1, the amino acid being a separate component not present in the Camu Camu particles.

7. The topical skin care composition of claim 1, the moisturizing pharmaceutically acceptable carrier comprising a plant-based butter and a plant-based oil.

8. The topical skin care composition of claim 1, the moisturizing pharmaceutically acceptable carrier comprising shea butter.

9. The topical skin care composition of claim 1, the surfactant being non-toxic.

10. The topical skin care composition of claim 1, the surfactant being sarcosine.

11. The topical skin care composition of claim 1, the composition being free of a second exfoliant.

12. The topical skin care composition of claim 1, the Camu Camu particles having an average particle size of about 50 to about 500 microns.

13. The topical skin care composition of claim 1, the composition being fragrance free.

14. A method for exfoliating the skin of a subject in need thereof, the method comprising: topically administering the composition of claim 1 onto the skin of the subject.

15. The method of claim 14, further comprising the step of applying water to the skin of the subject after administering the composition, the water being effective to dissolve the Camu Camu particles of the composition.

* * * * *